(12) United States Patent
Tachi et al.

(10) Patent No.: US 8,920,174 B2
(45) Date of Patent: Dec. 30, 2014

(54) ELECTRIC TACTILE DISPLAY

(75) Inventors: Susumu Tachi, Tokyo (JP); Hiroyuki Kajimoto, Tokyo (JP); Yonezo Kanno, Yotsukaido (JP)

(73) Assignees: The University of Tokyo, Tokyo (JP); Eye Plus Plus, Inc., Tokyo (JP)

(*) Notice: Subject to any disclaimer, the term of this patent is extended or adjusted under 35 U.S.C. 154(b) by 1813 days.

(21) Appl. No.: 12/096,447

(22) PCT Filed: Dec. 7, 2006

(86) PCT No.: PCT/JP2006/324439
§ 371 (c)(1),
(2), (4) Date: Mar. 2, 2010

(87) PCT Pub. No.: WO2007/066717
PCT Pub. Date: Jun. 14, 2007

(65) Prior Publication Data
US 2010/0151426 A1  Jun. 17, 2010

Related U.S. Application Data

(60) Provisional application No. 60/748,811, filed on Dec. 8, 2005.

(51) Int. Cl.
*G09B 21/00* (2006.01)
*G06F 3/01* (2006.01)
(Continued)

(52) U.S. Cl.
CPC ............ *G09B 21/003* (2013.01); *G09B 21/006* (2013.01); *A61B 5/11* (2013.01);
(Continued)

(58) Field of Classification Search
CPC .... G09B 21/00; G09B 21/001; G09B 21/003; G09B 21/004; G09B 21/006–21/008; A61F 4/00; A61F 9/08; A61G 2203/18; G06F 3/011; G06F 3/012; G06F 3/016; A61B 3/113; A61B 5/11; A61B 8/00; G02B 27/017; G08B 6/00

USPC .......... 434/113, 114; 340/4.11, 4.12; 341/21; 348/62; 382/114; 356/357; 623/4.1; 704/271

See application file for complete search history.

(56) References Cited

U.S. PATENT DOCUMENTS 3,349,489 A * 10/1967 Shackelford et al. ........... 433/32
3,752,929 A *  8/1973 Fletcher ........................ 704/231
(Continued)

FOREIGN PATENT DOCUMENTS

JP  2001-285679  10/2001
JP  2002-65721   3/2002
(Continued)

OTHER PUBLICATIONS

Electrotactile and Vibrotactile Displays for Sensory Substitution Systems, IEEE Transactions on Biomedical Engineering, vol. 38, No. 1, Jan. 1991.*

(Continued)

*Primary Examiner* — Nikolai A Gishnock
(74) *Attorney, Agent, or Firm* — Ladas & Parry, LLP (57) ABSTRACT

An electro-tactile display includes an electrode substrate provided with a plurality of stimulation electrodes, a conductive gel layer positioned between the stimulation electrodes and the skin of a wearer, a switching circuit section electrically connected to the stimulation electrodes, a stimulation pattern generating section electrically connected to the switching circuit, and means for alleviating a sensation experienced by the wearer as a result of the stimulation electrodes. In one aspect, the means for alleviating a sensation is configured from the conductive gel layer. The conductive gel layer has a resistance value equivalent to that of the horny layer of the skin. In another aspect, the means for alleviating a sensation is configured from the stimulation determination means and the threshold value adjustment means.

19 Claims, 7 Drawing Sheets

(51) Int. Cl.
*G08B 6/00* (2006.01)
*A61F 4/00* (2006.01)
*A61F 9/08* (2006.01)
*A61B 5/11* (2006.01)
*G02B 27/01* (2006.01)
*A61B 3/113* (2006.01)
*A61B 8/00* (2006.01)

(52) U.S. Cl.
CPC ............ *G06F 3/012* (2013.01); *G09B 21/001* (2013.01); *G02B 27/017* (2013.01); *G09B 21/004* (2013.01); *G08B 6/00* (2013.01); *G09B 21/007* (2013.01); *G06F 3/011* (2013.01); *G06F 3/016* (2013.01); *A61F 4/00* (2013.01); *A61G 2203/18* (2013.01); *A61B 3/113* (2013.01); *G09B 21/00* (2013.01); *A61B 8/00* (2013.01); *G09B 21/008* (2013.01); *A61F 9/08* (2013.01); *A61H 2201/1604* (2013.01); *A61H 2201/165* (2013.01)
USPC ........... 434/114; 340/4.11; 340/4.12; 341/21; 348/62; 382/114; 434/113; 623/4.1; 704/271

(56) References Cited

U.S. PATENT DOCUMENTS

| | | | | |
|---|---|---|---|---|
| 3,766,311 | A * | 10/1973 | Boll | 348/62 |
| 4,112,596 | A * | 9/1978 | Fletcher et al. | 600/590 |
| 4,287,895 | A * | 9/1981 | Hori | 600/590 |
| 4,520,501 | A | 5/1985 | DuBrucq | 704/271 |
| 4,697,601 | A * | 10/1987 | Durkee et al. | 600/590 |
| 4,980,917 | A * | 12/1990 | Hutchins | 704/254 |
| 5,212,476 | A * | 5/1993 | Maloney | 340/4.11 |
| 5,649,061 | A * | 7/1997 | Smyth | 706/16 |
| 5,689,246 | A * | 11/1997 | Dordick et al. | 341/21 |
| 5,794,203 | A * | 8/1998 | Kehoe | 704/271 |
| 5,853,005 | A * | 12/1998 | Scanlon | 600/459 |
| 5,878,154 | A * | 3/1999 | Schimmelpfennig | 382/114 |
| 6,343,269 | B1 * | 1/2002 | Harada et al. | 704/243 |
| 6,430,450 | B1 | 8/2002 | Bach-y-Rita et al. | |
| 6,707,236 | B2 * | 3/2004 | Pelrine et al. | 310/311 |
| 6,712,613 | B2 * | 3/2004 | Depta | 434/114 |
| 7,333,020 | B2 * | 2/2008 | Cohen et al. | 340/573.1 |
| 7,629,897 | B2 * | 12/2009 | Koljonen | 340/4.13 |
| 8,044,766 | B2 * | 10/2011 | Ghovanloo et al. | 340/4.11 |
| 8,068,644 | B2 * | 11/2011 | Tkacik | 382/114 |
| 8,140,143 | B2 * | 3/2012 | Picard et al. | 600/382 |
| 8,547,341 | B2 * | 10/2013 | Takashima et al. | 340/407.2 |
| 2007/0016425 | A1 * | 1/2007 | Ward | 704/271 |
| 2007/0211947 | A1 * | 9/2007 | Tkacik | 382/232 |
| 2008/0188777 | A1 * | 8/2008 | Bedziouk et al. | 600/595 |
| 2012/0016472 | A1 * | 1/2012 | Chen et al. | 623/4.1 |

FOREIGN PATENT DOCUMENTS

| | | |
|---|---|---|
| JP | 2002-65866 | 3/2002 |
| JP | 2002-328596 | 11/2002 |
| JP | 2006-78429 | 3/2006 |
| WO | 01/38958 | 5/2001 |

OTHER PUBLICATIONS

Konyo, M., et al., "Tactile Feeling Display for Touch of cloth Using soft High Polymer Gel Actuators," TVRSJ vol. 6, No. 4, pp. 323-328 (2001).

* cited by examiner

PREVIOUS FRAME    CURRENT FRAME    TIME DIFFERENTIAL

PREVIOUS FRAME    CURRENT FRAME    TIME DIFFERENTIAL

FIG.14

CURRENT FRAME

PREVIOUS FRAME → COMPENSATED "PREVIOUS FRAME" → TIME DIFFERENTIAL

HEAD ROTATION INFORMATION

ORIGINAL IMAGE     PROCESSED IMAGE

ELECTRIC TACTILE DISPLAY

RELATED APPLICATION

The present invention is based on provisional application No. 60/748,811 filed in the US on Dec. 8, 2005, and claims the benefits thereof. The contents of the aforementioned application are herein incorporated in this specification in their entirety by reference.

TECHNICAL FIELD

The present invention relates to an electro-tactile display.

BACKGROUND ART

Figure 1:
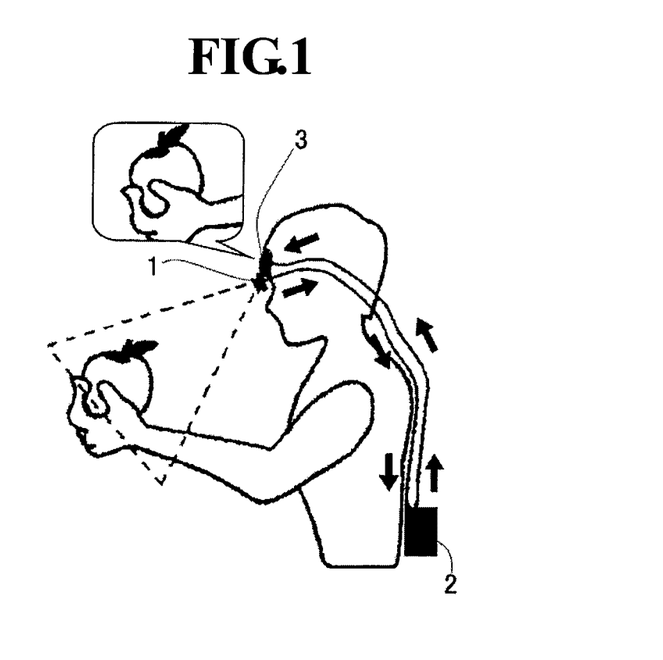
FIG. 1 is a view of a forehead-mounted electrical stimulation system.

A configuration for a forehead-mounted electro-tactile display is shown in FIG. 1. The system includes a sensor (camera) 1 that acquires environmental information mounted on a head, an arithmetic section 2 that processes this information and generates a tactile presentation signal, and an electrical stimulation presentation section 3 fitted to the forehead and provided with an electrode matrix that generates sensory stimuli. A compact camera fitted to, for example, sunglasses, captures the frontal view of the wearer. Images of the view captured by the compact camera are converted into tactile information resulting from electrical stimulation by the arithmetic section. The wearer of this system can acquire environmental information as a result of tactile stimulation received via the forehead. The system then functions as a proxy system that brings about sight through the tactile sensation in case that the sensor is an image sensor and the wearer is, for example, a person with impaired vision. Namely, the forehead-mounted electro-tactile display provides an FRS (Forehead Sensory Recognition System). By passing through an appropriate training program, the FRS can function as an artificial retina for the visually impaired without any surgery being required.

The basic theory of electrical stimulation is disclosed in Japanese Unexamined Patent Publication No. 2002-65866 "COMPOSITE ELECTRODE USED IN ELECTRICAL STIMULATION", Japanese Unexamined Patent Publication No. 2002-328596 "TACTILE PRESENTATION METHOD AND DEVICE", and International Patent Publication No. WO01/038958 "TACTILE PRESENTATION METHOD AND DEVICE EMPLOYING ELECTRICAL STIMULATION". Electrical stimulation to the forehead is disclosed in Japanese Unexamined Patent Publication No. 2001-285679 "IMAGE RECOGNITION DEVICE FOR THE BLIND". Similar technology "TONGUE PLACED TACTILE OUTPUT DEVICE" is given in U.S. Pat. No. 6,430,450B1. The contents of the aforementioned documents are herein incorporated in this specification by reference.

However, the related technologies described in the above applications merely relate to an electrical stimulation, or the basic idea of a sensory proxy that presents tactile sensations on a person's forehead, and do not resolve the actual problems in practical terms.

The present invention has resolved several problems that appeared during implementation tests by actually constructing a forehead-mounted electrical stimulation system. Many of the problems to be resolved by the present invention are caused by the device being "forehead-mounted". One problem is of the wearer experiencing pain and discomfort when electrical stimulation is applied. An electro-tactile presentation display typically electrically stimulates the skin of fingertips. However, the skin on a person's forehead is thin compared to the skin on the fingertips. This means that if the same electrical stimulation as for the fingertips is carried out, the wearer will experience pain and information cannot be presented. This also applies to the electrical stimulation of body parts (breast, back, abdomen, etc.) other than the forehead where the skin is relatively thin compared to the skin of the fingertips.

Further, with a forehead-mounted electro-tactile display, a large number of electrodes are densely arranged compared to electro-tactile displays for use with fingertips. When the number of stimulation points is increased, the scanning time becomes excessive and the overall stimulation frequency falls. It is known that when the stimulation frequency falls below a certain value (for example, 30 Hz), a "coarse feeling" characteristic of stimulation occurs, and the wearer experiences a strong feeling of unpleasantness. This problem also applies to the case of the electrical stimulation of body parts (breast, back, abdomen, etc.) other than the forehead of a wider area than the surface area of the fingertips where a large number of electrodes arranged at high-density are used. The object is therefore to generate electrical stimuli that feel pleasant.

It is a further object of the present invention to provide a forehead-mounted electrical stimulation presentation board appropriate for the curvature of a person's forehead. This object is also applicable to electrical stimulation presentation boards fitted to other parts similar to a person's forehead where the Gaussian curvature is not zero. Other objects to be resolved by the present invention will become apparent from the description of the specification described in the following.

DISCLOSURE OF THE INVENTION

The present invention provides an electro-tactile display including an electrode substrate provided with a plurality of stimulation electrodes, a conductive gel layer positioned between the stimulation electrodes and the skin of a wearer, a switching circuit section electrically connected to the stimulation electrodes, a stimulation pattern generating section electrically connected to the switching circuit, and means for alleviating a sensation experienced by the wearer as a result of the stimulation electrodes.

The plurality of stimulation electrodes are typically electrodes in the shape of a matrix or arrayed electrodes that comprise a plurality of electrodes arranged in series in transverse and vertical directions (x and y directions). In one mode, the conductive gel layer is provided directly on the surface so as to cover the surface (surface where the stimulation electrodes are formed) of an electrode substrate. In one aspect, another conductive layer can be interposed between the surface of the electrode substrate and the conductive gel layer. Alternatively, another conductive layer can be provided between the conductive gel layer and the skin. In a preferred mode, the electro-tactile display is a forehead-mounted electro-tactile display. However, it is also made apparent in the description that the present invention is also applicable for electro-tactile displays other than forehead-mounted electro-tactile displays.

In a preferred mode, the means for alleviating a sensation is configured from the conductive gel layer. The conductive gel layer has a resistance value equivalent to that of the horny layer of the skin. The thickness of the conductive gel layer is preferably 0.3 to 2.0 millimeters. When the thickness of the conductive gel layer is less than 0.3 millimeters, the wearer experiences extremely severe pain. When the thickness of the conductive gel layer is thicker than 2.0 millimeters, the sensation does not occur. The thickness of the conductive gel layer is preferably 0.5 to 1.0 millimeters. In this range, particularly comfortable electrical stimulation is provided to the wearer.

In a preferred mode, the electro-tactile display includes stimulation determination means that determine whether or not to carry out electrical stimulation based on a threshold value of a stimulation determination function, and threshold value adjustment means that adjusts the threshold value of the stimulation determination means. The means for alleviating a sensation is then configured from the stimulation determination means and the threshold value adjustment means. The threshold value adjustment means changes the threshold value so that the number of times of stimulation occurring in a fixed time period does not exceed a predetermined maximum number of stimuli. It is then possible to provide the target stimulation frequency by controlling the threshold value. It is preferable to ensure that the stimulation frequency is at least 30 Hz or more by suppressing the total number of stimuli occurring in a fixed time period. Further, in a preferred mode, an intermediate gradation representation is implemented by increasing the number of times of stimulation at one point in a fixed time period.

In a preferred mode, an electrical stimulation presentation board of the electro-tactile display is comprised of an electrode substrate provided with a plurality of stimulation electrodes on a surface thereof, a conductive gel layer provided at the surface side of the electrode substrate, and a switching circuit section provided at the reverse side of the electrode substrate. The electrical stimulation presentation board is electrically connected to a control unit of the electro-tactile display (including a stimulation pattern generating section) and a power supply. The conductive gel layer is directly or indirectly (via another member) provided at the surface side of the electrode substrate. The switching circuit section is directly or indirectly (via another member) provided at the rear surface side of the electrode substrate. Here, the rear surface side of the electrode substrate means the opposite side to the side where the electrodes are provided.

In a preferred mode, the electrode substrate is a flexible substrate. At least one cut is preferably formed in the flexible substrate. The electrical stimulation presentation board can be configured to match with the curved surface of a forehead etc. as a result of the flexible substrate preferably being provided with one or more cuts. More specifically, in one aspect, a plurality of regions are defined by forming a plurality of cuts in transverse and vertical directions so as to leave the edges of the flexible substrate.

A predetermined number of electrodes are provided at each region. Still more preferably, a set of a switching circuit and a communication circuit is provided for each region. Communication wiring for each communication circuit is then provided at the edges. More specifically, in a further mode, the flexible substrate includes a plurality of strip-shaped regions extending in a longitudinal direction of the electrical stimulation presentation board, with a predetermined number of electrodes being provided at each strip-shaped region.

In a preferred mode, the electrical stimulation presentation board is provided with one or more elastic layers positioned at the surface side and/or the rear surface side of the electrode substrate. It is also possible to provide superior adaptability with the curved surface of a person's forehead etc. by providing the elastic layer at the electrical stimulation presentation board. The elastic layer is exemplified by an anisotropically conductive elastic layer provided at the surface of the electrode substrate. In this case, the electrical stimulation presentation board comprises a stimulation electrode substrate, an anisotropically conductive elastic layer provided so as to cover the surface of the stimulation electrode substrate, and a conductive gel layer provided on the anisotropically conductive elastic layer. The stimulation electrodes then supply electrical stimulation to the skin via the anisotropically conductive flexible layer and the conductive gel layer. Alternatively, the electrical stimulation presentation board comprises a stimulation electrode substrate, a conductive gel layer provided so as to cover the surface of the stimulation electrode substrate, and an anisotropically conductive elastic layer provided on the conductive gel layer. The stimulation electrodes then supply electrical stimulation to the skin via the conductive gel layer and the anisotropically conductive elastic layer. The elastic layer provided at the rear side of the electrode substrate does not have to be conductive. When the elastic layer is provided at the rear side of the electrode substrate, the electrode substrate is preferably a flexible substrate.

In one mode, the switching circuit section is provided at the flexible substrate. In a specific example, the electrical stimulation presentation board includes a flexible substrate provided with stimulation electrodes, and an elastic layer provided at the rear surface side of the flexible substrate. A portion of the flexible substrate (the portion with no stimulation electrodes) is folded to extend to the rear surface side of the elastic layer and a switching circuit section is provided at the folded and extended section of the flexible substrate. In a further mode, the electrical stimulation presentation board includes a circuit substrate that is independent of the flexible substrate. The switching circuit section is then provided at the circuit substrate. In a specific example mode, the electrical stimulation presentation board includes a flexible substrate having stimulation electrodes, an elastic layer provided at the rear surface side of the flexible substrate, a circuit substrate independent of the flexible substrate provided at the rear surface side of the elastic layer, and a switching circuit provided at the rear surface side of the circuit substrate.

In a preferred mode, the electro-tactile display includes means for measuring stimulation voltage and means for adjusting power supply voltage. The power supply voltage is set to a voltage a predetermined voltage V higher than the measured stimulation voltage by the power supply voltage adjusting means.

In a preferred mode, the electro-tactile display is a forehead-mounted electro-tactile display. The display includes means for emphasizing stimulation at time-varying locations. This means cancels changes to images caused by movement of the wearer and emphasize an object moving in an external environment.

In a preferred mode, the electro-tactile display includes means for detecting depth, and presents sensations depending on distance.

BRIEF DESCRIPTION OF THE DRAWINGS

FIGS. 6A, 6B, and 6C are views showing a configuration where stimulation electrodes are arranged on a strip-shaped flexible substrate, where.

DETAIL DESCRIPTION OF THE INVENTION

[A] Electro-Tactile Presentation Apparatus (Electro-Tactile Display)

[A-1] Electro-Tactile Presentation Apparatus

A description is now given of one aspect of an electro-tactile presentation apparatus that forms the basis of the present invention. The electro-tactile presentation apparatus includes stimulation electrodes, a switching circuit, a control section (mainly constituted by a computer), and a current source. The stimulation electrodes are an electrode array or an electrode matrix comprised of a plurality of electrodes arranged in transverse and vertical directions (x and y directions). Each of the electrodes constituting the electrode array and the current source are electrically connected via a switching circuit. Current source electrodes in the stimulation electrodes are then selected using a control signal from the control section (stimulation pattern generator) and are supplied with current. Stimulation is then performed from the electrodes to which current is supplied. The electrodes are preferably from 0.5 millimeters to 2.0 millimeters in diameter, and are typically 1.0 millimeters. The electro-tactile presentation apparatus switches connections of each electrode and the current source and connections of each electrode and ground over time. The electrode array presents information by changing the selection of electrodes at positions for stimulation and ground electrodes. The switching of the connections of the current source and ground is carried out by a switching circuit (for example, a half-bridge circuit). Selection of the electrodes for stimulation and the ground electrode is carried out by the control section. An electrical circuit is then formed with underneath the skin by connecting electrodes of locations for stimulation to a current source and connecting other electrodes to ground and nerves are then stimulated. Further, the electrode array presents surface information by switching stimulation points (selection of electrodes at positions for stimulation) over time.

The electro-tactile presentation apparatus further has an environment information acquisition section. The environment information is typically a scene. Image information is acquired by an image sensor (for example, a camera) and inputted. A tactile presentation signal is then generated based on the inputted image information. In a preferred embodiment, the image sensor is mounted on a person's head (this includes mounted on spectacles or sunglasses worn on a person's head). Light used by the image sensor to acquire image information is by no means limited to visible light, and, for example, an infrared camera employing infrared light is also possible. The acquired environment information is processed by the control section. The control section then outputs a tactile presentation signal (control signal) for presenting certain stimulation pattern information to the switch circuit. Tactile stimulation is then generated from the electrode array by the switching circuit. In a preferred mode, the electro-tactile presentation apparatus is a forehead-mounted electro-tactile presentation apparatus that provides an FRS system. The forehead-mounted electrical stimulation presentation apparatus comprises a forehead-mounted electrical stimulation presentation board suited to the curvature of a person's forehead.

[A-2] FRS System

The FRS (Forehead Sensory Recognition System) uses technology that takes the tactile sensation occurring at a person's forehead as a substitute retina. Sensory proxies using electrical stimulation have been proposed since the 1960's but the method of taking the forehead as a stimulated portion is relatively new. Using the forehead as a stimulated portion is rational. Wearing items on the forehead is easy and conversion of the coordinate system within the brain is straightforward compared to the case of wearing on other parts of the body. A compact camera fitted to, for example, sunglasses, captures the frontal view of the wearer. In the FRS system, an image for a view taken by a compact camera is converted to tactile information using electrical stimulation. The tactile information is then supplied to the wearer. The image information acquired by the camera is converted to tactile information through two processes. In a first process, spatial contour extraction is carried out in order to enhance the contour information. In a second process, temporal band-pass filtering is carried out in order to enhance time-varying information. FRS can therefore easily analyze images by simulating the pre-processing of an actual visualization system. Through an appropriate training program, the FRS can function as an artificial retina for the visually impaired without any surgery being required.

[B] Configuration of Forehead-Mounted Electrical Stimulation Presentation Board Suited to the Curvature of a Person's Forehead

[B-1] Problems with Forehead-Mounted Electrical Stimulation Presentation Board of the Related Art The forehead-mounted electrical stimulation presentation board of the related art does not describe a specific method for arranging an electrode matrix on a person's forehead. However, if the electrode substrates are simply arranged on a person's forehead, there are the problems that: this is not appropriate for the curvature of a person's forehead; and that the amount of cabling required to extend to each of the electrodes when the number of electrodes is increased is problematic.

Figure 2:
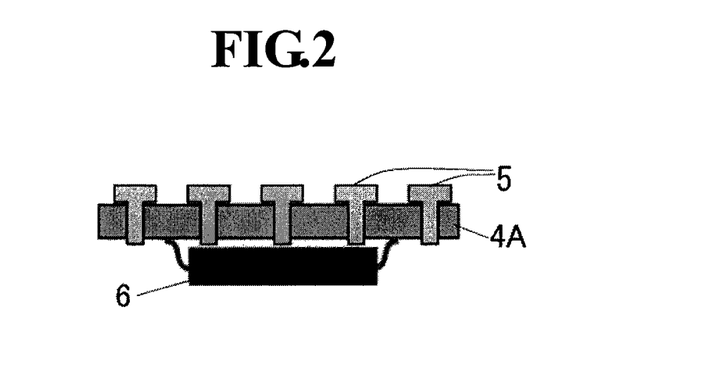
FIG. 2 is a view showing integration of an electrode substrate and switching circuit, and a serial communication circuit.

We therefore propose the followings. First, a stimulation electrode substrate shall be configured as follows. Electrical stimulation electrodes 5 are exposed at the surface of the substrate 4A. A circuit element 6 including a switching circuit for selecting electrodes to be stimulated and a communication circuit is then mounted on the rear surface side of the substrate 4A (FIG. 2). The wiring on the substrate can be dramatically reduced by locating the electrodes and the switching circuit in close proximity. The number of wires between the forehead stimulation electrode substrate and a stimulation current generating circuit worn on another part of the body can then be kept at a fixed amount or less by carrying out communication of instruction signals to the switching circuit (this is typically wired serial communication or wireless communication).

Figure 3:
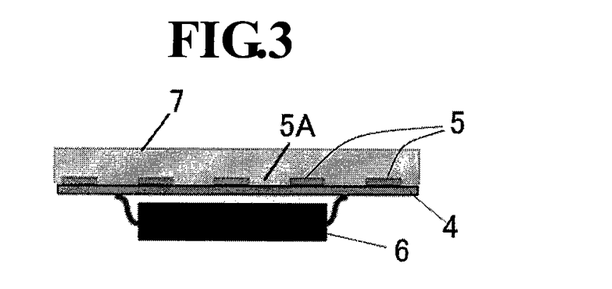
FIG. 3 is a view showing an electrode substrate employing a flexible substrate.

[B-2] Configuration for Forehead-Mounted Electrical Stimulation Presentation Board Employing a Flexible Substrate and Conductive Gel A flexible substrate 4 is adopted as the substrate so that the substrate is lightweight and suited to the shape of a person's forehead (FIG. 3). Polyimide film that is currently most typically used can be considered as a material for the flexible substrate but it is also possible to use an elastic film employing a material having elasticity such as silicon rubber, or a type of film that employs a thermoplastic resin and can be molded through the application of heat after wiring the substrate. In particular, the curvature of a person's forehead can be determined to a certain extent. A material that can be molded along the curvature is therefore preferable and a thermoplastic resin is the candidate. Electrode pins 5 are formed on land (exposed portions for soldering use) of the flexible substrate 4 using gold plating processing 5A.

A conductive gel layer 7 is provided on the electrode pins 5 formed on the flexible substrate 4. Hydrogel (where water and an electrolyte are suspended in hydrophilic resin) that is currently commonly used in electrical stimulation as a conductive gel can be considered. This conductive gel layer is not just for maintaining electrical contact between the electrodes and the skin, but is also for preventing focusing of current within the skin and preventing pain caused by the current.

The following is a description of a function of the conductive gel layer. First, pain sense nerves that generate a sense of pain, and tactile nerves that generate senses of vibration and pressure exist under the skin. The thickness of a nerve axon is in the order of one micrometer to five micrometers, respectively. With electrical stimulation from the skin, a potential difference between membranes fluctuates as a result of a potential distribution surrounding nerve axons to causes nerve activity. It is known that if the distance from the skin surface to the nerve axons is fixed, a current threshold value that causes nerve activity is inversely proportional to the thickness of the nerve axons or inversely proportional to the square root of the thickness. This means that the tactile nerves are easier to stimulate than the pain sense nerves, and that it is possible to achieve tactile sensation without pain occurring. However, in reality the distance from the surface of the skin to the nerve axons is not fixed and the electrical resistance distribution of the skin is also not fixed. This means that situations occur where the current becomes localized so that pain sense nerves are stimulated. In order to diminish this problem, electrically conductive gel is interposed between the electrodes and the skin. Focusing of the current can then be prevented as a result of the current being diffused by the gel layer.

Figure 2A:
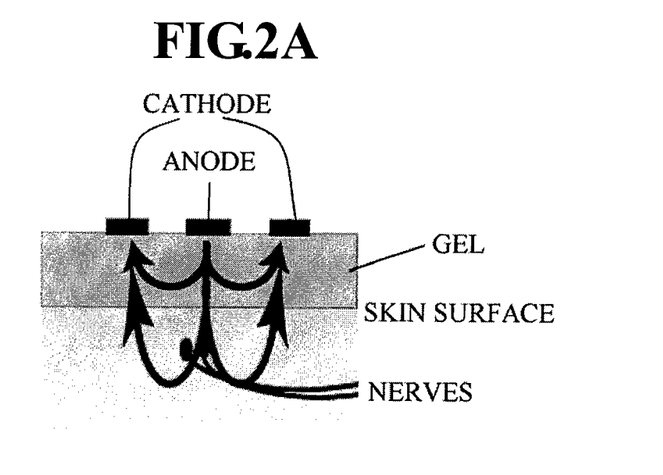
FIG. 2A is a view illustrating electrical stimulation when conductive gel is provided between electrodes and the skin.

The following four relationships exist between the four items of the thickness of the conductive gel, the distance between an anode and a cathode, gel impedance, and impedance of the skin (refer to FIG. 2A).

(1) When the gel impedance is relatively low compared to the skin impedance, a current path is formed within the gel layer and reaching the skin is difficult. This means that the majority of consumed power is taken up in the generation of Joule heat at the gel layer and is an extremely critical problem for a portable tactile presentation device.

(2) When the thickness of the gel is large compared to the gap between the electrodes, a current path is similarly formed within the gel layer and it is difficult to reach the skin.

(3) When the gel is thin, it becomes easy for pain to occur because the effect of diffusing the current is reduced.

(4) When the impedance of the gel is large, the majority of the consumed power is consumed in the generation of joule heat at the gel layer.

With the transcutaneous electrical stimulation of the related art, forming a current path within the gel layer was not a big problem because there was sufficient distance between the anodes and cathodes (an electrode gap of 5 millimeter or more). A conductive gel of a low resistance (10 to 50 KΩcm, typically 20 KΩcm) was used in order to deal with the above problem (3). However, when a large number of electrodes are arranged densely as on the present occasion (an electrode gap of 1 millimeter to 5 millimeter), an optimum resistance setting is newly required so as to keep the forming of a current path within the conductive gel layer to a minimum and to prevent occurring of pain by diffusing of the current.

In order to achieve this role, we found that when the conductive gel has a thickness of 0.3 millimeters to 2.0 millimeters with an optimum thickness of approximately 0.5 millimeters to 1.0 millimeter, and the resistance value of the gel is a high resistance value (100 to 1000 KΩcm, and typically 400 KΩcm) that is the same order as for the skin, optimum stimulation can be carried out without pain being caused while keeping the consumed power to a minimum.

The gel is not required in the case of electrical stimulation to the fingertips. A bulky (0.5 millimeter to 1.0 millimeter) high-resistance horny layer exists at the fingertip skin so as to bestow the current diffusion effects described above. In the electrical stimulation of people's foreheads, when the gel layer was not provided, we confirmed that use of the device was completely not possible due to a sense of pain. Further, when a gel layer of a low resistance typically used in the electrical stimulation was used, we confirmed that it was difficult for a sensation to occur.

To conclude, a conductive gel layer is provided detachably at the stimulation electrode substrate so as to cover the stimulation electrode substrate. The electrical stimulation section includes a stimulation electrode substrate and a conductive gel layer provided detachably at the side of the stimulation electrode substrate where the electrodes are provided. The stimulation electrodes supply electrical stimulation to the skin (forehead) via the conductive gel layer. The conductive gel preferably has a resistance value equivalent to that of the horny layer of the skin. Preferably, the thickness of the conductive gel layer is 0.3 to 2.0 millimeters. The thickness of the conductive gel layer is more preferably 0.5 to 1.0 millimeters.

Figure 4:
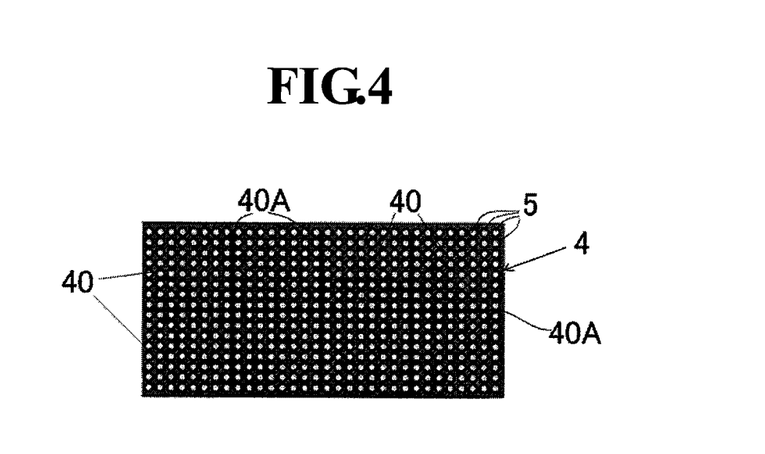
FIG. 4 is a view showing a flexible substrate equipped with cuts.
Figure 5:
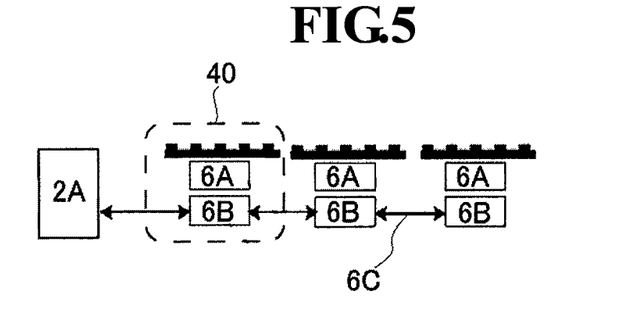
FIG. 5 is a view showing circuit elements of each region defined in FIG. 4; A switching circuit and a communication circuit are present each one region, and data is exchanged through communication between regions.

Next, a description is given of an electrical stimulation presentation board suited to the curvature of a person's forehead. Flexible substrates currently used can be easily bent but cannot be expanded or contracted. Application as is to surfaces where the Gaussian curvature is not zero such as with a person's forehead is therefore not possible. Further, recently developed substrates employing thermoplastic resins can be deformed in a manner including compression and expansion by applying heat but matching completely with the shape of a specific forehead of an individual wearer is difficult. The conductive gel layer described above absorbs indentations of the skin to a certain extent as a result of being elastic. However, the optimum thickness of the conductive gel layer is determined depending on other requirements as described previously. The extent to which a role appropriate for the shape of a forehead can be achieved is therefore restricted. Adaptability to the curvature of a person's forehead can therefore be achieved by inserting cuts into the substrate. Wiring on the substrate is therefore substantially restricted by the cuts. A first candidate is a technique where, as shown in FIG. 4, the whole body is formed from a large flexible substrate 4, with inner cuts 40A therein. In the case of this example, 512 points overall are divided into eight regions 40 of 4×2, with electrodes for sixty-four points existing at one region 40. As shown in FIG. 5, one set of a switching circuit 6A and a communication circuit 6B corresponds to electrical stimulations at 64 points. This ensures that the cuts 40A of the flexible substrate 4 do not disturb the most complex "wiring from the switching circuit 6A to each of the electrodes 5". The "communication circuit 6B" referred to here is that connecting between the stimulation pattern generation section 2A, the sixty-four point stimulation generation section, and sixty-four point stimulation generation sections (FIG. 5).

Figure 6A:
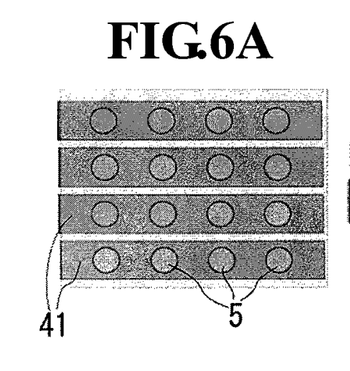
FIG. 6A is a plan view of the essential parts of an electrical stimulation presentation board.
Figure 6B:
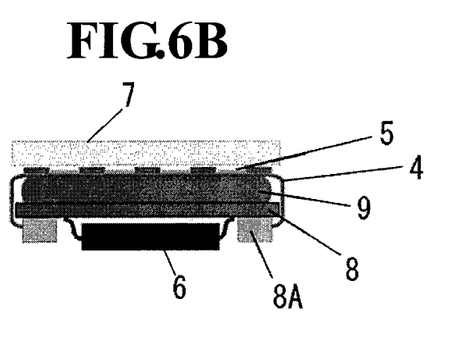
FIG. 6B is a cross-sectional view of the same.
Figure 6C:
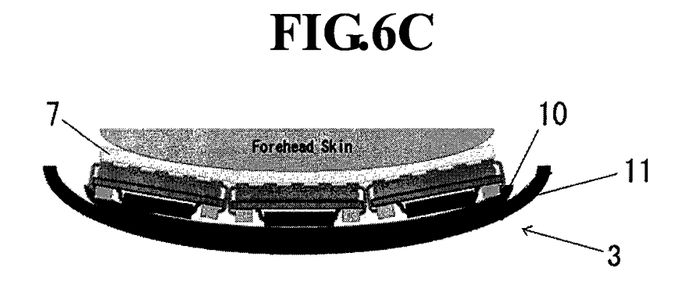
FIG. 6C is a cross-sectional view showing the whole of an electrical stimulation presentation board.

The second candidate is a method of arranging the stimulation electrodes 5 in a row at a thin belt-shaped flexible substrate 41 (FIG. 6). The substrate mounted with the electric circuit element (hereinafter referred to as the circuit substrate) 8 and the flexible substrate 4, i.e. the belt-shaped flexible substrate (hereinafter referred to as the electrode substrate) 41 are connected by a connector 8A. Stimulation electrodes 5 are then formed on the electrode substrate. Each strip of the electrode substrate 41 can be curved and can shift to the left and right. It is therefore possible to achieve adaptability to the forehead shape that is close to being spherical, i.e. where the Gaussian curvature is not zero. It is preferable for an elastic layer 9 to be provided between the electrode substrate 4 and the circuit substrate 8. Silicon rubber and urethane foam etc. can be considered as the elastic layer 9. In particular, urethane foam is the prominent candidate because it has been applicable to a pillow etc. that can be adapted to the shape of a person's forehead. It is also preferable for friction at the interface of the elastic layer 9 and the electrode substrate 4 to be low. It is further preferable for a lubricant or a lubricating coating to be applied to the flexible substrate surface or the elastic layer surface, or to both. In FIG. 6, electrodes are arranged in a row on each one strip of the flexible substrate but pluralities of rows can also be provided.

Figure 7A:
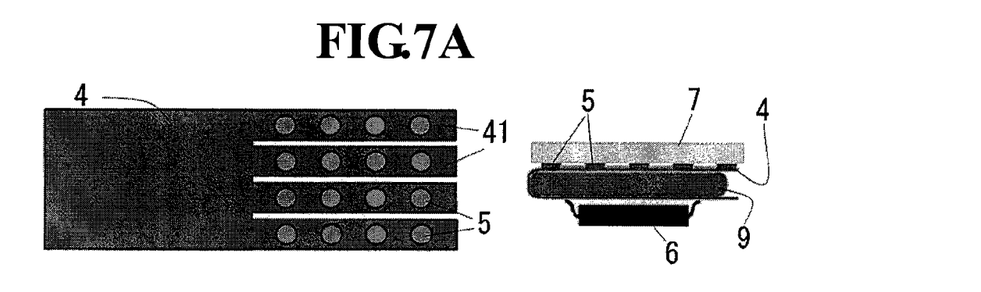
FIGS. 7A, 7B and 7C are views showing a configuration where an electrode substrate and a circuit substrate are integrated.
Figure 7B:
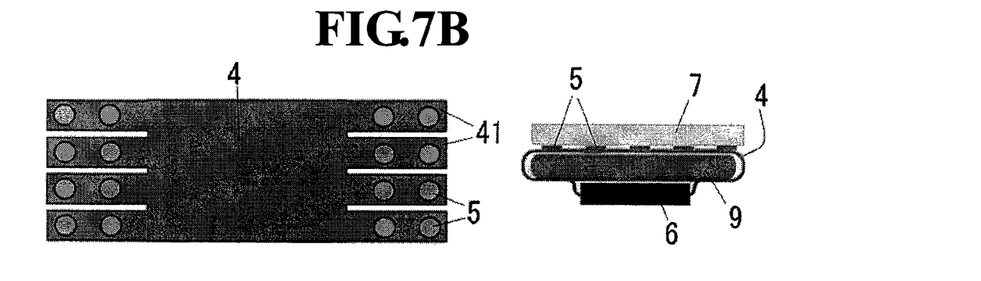
Figure 7C:
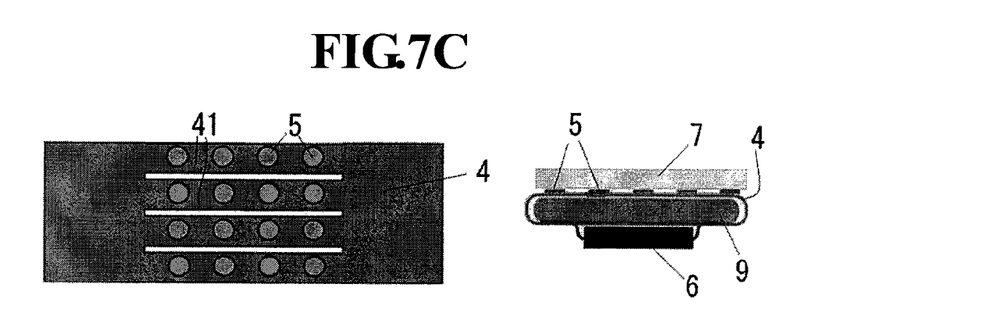

According to the method described above, the circuit substrate 8 and the electrode substrate 4 are separate and connected by the connector 8A but integration of the circuit substrate 8 and the electrode substrate 4 can also be considered. A method for this is given in FIG. 7. The electrode portion is the strip-shaped flexible substrate 41 but the portion the electrical circuit elements are mounted on can be the same flexible substrate or can be backing on a stiff plate. In recent substrate fabrication technology, it is possible to make a flexible substrate and a usual stiff substrate in a coupled manner and the adoption of this technology is also possible.

To conclude, the electrical stimulation presentation board can be made lightweight by integrating the stimulation electrode substrate, the switching circuit, and the communication circuit. In a specific example, the electrical stimulation presentation board includes a stimulation electrode substrate provided with stimulation electrodes where the stimulation electrodes are provided on the surface of the stimulation electrode substrate. A switching circuit for selecting stimulation electrodes providing stimulation and a communication circuit are provided on the rear surface side of the stimulation electrode substrate. In one mode, the switching circuit and the communication circuit are comprised of ICs. The switching circuit is electrically connected to each electrode of the stimulation electrode substrate and is electrically connected to the control section via the communication circuit. In one mode, the circuit substrate having the switching circuit is electrically connected to the stimulation electrode substrate via a connector but the circuit substrate and the stimulation electrode substrate can also be formed integrally. In one mode, the electrical stimulation presentation board can be fitted to a person's forehead by coupling the rear side to the headband 11 via an elastic body 10 (FIG. 6C).

The stimulation electrode substrate is formed in a curved shape along the shape of a person's forehead or can be formed so as to be capable of curving. In one mode, the electrode substrate is comprised of a plurality of small area substrates, with a curved shape being formed by adjusting orientation of each small area substrate and connecting the small area substrates. In a further mode, the stimulation electrode substrate is comprised of a plurality of small area sections (divided into a plurality of portions) and the orientation of each small area section can be changed. The stimulation electrode substrate with a curved shape along the curve of a person's forehead is then formed by changing the orientation of each small area section. The small area sections are independent to each other and can be connected so as to change the orientation of the small area section. However, in a preferred embodiment, a plurality of small area sections can be formed by forming one or more cuts in one flexible substrate. The shape of the small area section is not limited but in a preferred mode is exemplified by a rectangular shape or a strip shape.

The stimulation electrode substrate is preferably comprised of a flexible substrate having a plurality of electrodes. In a further mode, at least one cut is formed in the flexible substrate. It is possible for the cuts to intersect but it is also possible for a number of cuts to be provided without intersection (for example, a plurality of cuts can be provided in parallel in one direction only).

In a specific mode, a plurality of cuts are formed in transverse and vertical directions in a transverse rectangular flexible substrate with leaving edges thereof so that a plurality of rectangular regions are defined on a single flexible substrate. A predetermined number of electrodes are provided at each defined region. The cuts can be made not to influence the wiring from the switching circuit to each of the electrodes by providing one set of a switching circuit and a communication circuit for each region. Further, by forming cuts so that the edges remain, it is possible to carry out communication wiring (Inter-unit communication channel wiring) 6C by utilizing the edges (FIG. 5).

In a specific mode, at a stimulation electrode substrate comprised of a transverse rectangular flexible substrate 4 defining a longitudinal direction and a short side direction, a plurality of strip regions 41 are formed by forming a plurality of cuts of a predetermined length in a longitudinal direction (preferably in parallel) from one short side, with a predetermined number of electrodes 5 then being provided at each strip region (FIG. 7A). In a further example mode, a plurality of strip-shaped regions 41 are formed by making a plurality of cuts of predetermined lengths from the short sides at both sides (preferably in parallel) and providing a predetermined number of electrodes 5 at each strip region (FIG. 7B). In a still further example mode, a plurality of strip-shaped regions 41 are formed by making a plurality of cuts of predetermined lengths in a longitudinal direction at a central portion in the longitudinal direction (preferably in parallel) and providing a predetermined number of electrodes 5 at each strip region (FIG. 7C). The flexible substrate 4 formed with cuts in the longitudinal direction then has the portion where the cuts are formed (the portion having the electrodes) on the surface side and is mounted on the elastic body 9 so as to provide the electrical stimulation presentation board. In one mode, a (not flexible) substrate is provided at the rear surface side of the elastic body. The circuit element is then arranged at the rear surface side of the substrate. The portion where the cuts of the flexible substrate constituting the stimulation electrode substrate are formed is then electrically connected to the circuit elements via a connector provided at the substrate. In a further mode, the portion where the cuts of the flexible substrate constituting the stimulation electrode substrate are not formed is connected integrally to the circuit element or the circuit substrate.

[B-3] Configuration Employing an Anisotropically Conductive Layer

The conductive gel layer described above absorbs indentations of the skin to a certain extent as a result of being elastic. However, the optimum thickness is determined depending on other requirements and the extent to which a role appropriate for the shape of a forehead can be achieved is therefore restricted to 0.5 millimeters to 1.0 millimeters. In the case of an elastic layer where current only passes in a thickness direction, it is possible to increase the thickness of the elastic body as a whole by providing this layer between the electrodes and gel.

Figure 8:
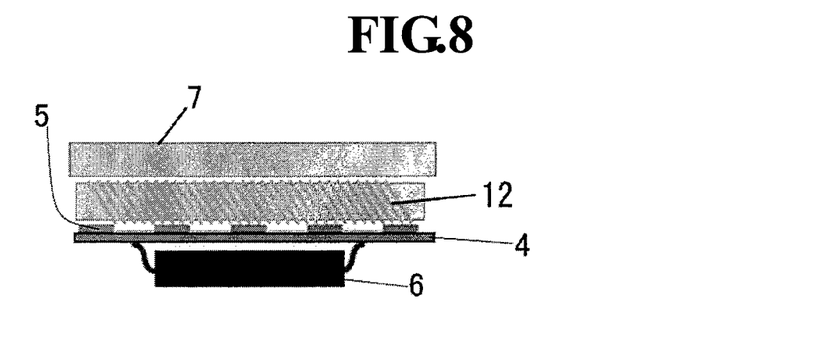
FIG. 8 is a view showing a situation where an elastic layer having anisotropically conductive properties is interposed between an electrode substrate and a gel layer.

Anisotropic conductivity means that electrical resistance possesses anisotropy. A typical example product is anisotropically conductive rubber where metal wire is densely embedded in the thickness direction of a rubber plate. The current passes in a thickness direction of the rubber plate but does not travel in a direction orthogonal to the thickness. An elastic layer 12 that is anisotropically conductive is interposed between the electrode substrate 4 and the gel layer 7 or between the gel layer and the skin. The anisotropically conductive layer 12 deforms as a result of pressure when the electrodes are pressed onto the forehead and adapts to the shape of the forehead. As a result, it is possible to keep deformation of the electrode substrate to a minimum. Damage due to fatigue of the electrode substrate and restrictions on the design can therefore be diminished.

To summarize, it is possible to adopt an anisotropically conductive layer (for example, anisotropically conductive rubber) as an element for the electrical stimulation presentation board. The stimulation electrode substrate is preferably a flexible substrate but is not limited to being the flexible substrate. In one mode, the electrical stimulation presentation board includes a stimulation electrode substrate, an anisotropically conductive elastic layer (for example, anisotropically conductive rubber) provided so as to cover the stimulation electrode substrate, and a conductive gel layer provided on the anisotropically conductive elastic layer. The stimulation electrodes then supply electrical stimulation to the skin (forehead) via the anisotropically conductive elastic layer and the conductive gel layer. In a further aspect, the electrical stimulation presentation board includes a stimulation electrode substrate, a conductive gel layer provided so as to cover the stimulation electrode substrate, and an anisotropically conductive elastic layer (for example, anisotropically conductive rubber) provided on the conductive gel layer. The stimulation electrodes then supply electrical stimulation to the skin (forehead) via the conductive gel layer and the anisotropically conductive elastic layer.

[C] Techniques for Reducing Power Consumption

[C-1] Problems with Electrical Stimulation Circuits of the Related Art

As described for the optimum design for the thickness of the gel and the impedance, reduction of the power consumption is also a very important object for a portable electrical stimulation device. Power consumption of the arithmetic/logic sections is not a major problem. However, a high voltage in the order of one hundred to four hundred volts is required for electrical stimulation and the power consumption of the analog circuitry for generating this voltage and controlling the current is therefore the most substantial.

[C-2] Control of the Voltage of the Power Supply by Using Voltage Information Measured at the Stimulation Electrodes Regarding the electrical stimulation, an important parameter for causing tactile sensation is current rather than voltage and the stimulation circuit therefore carries out current control. The stimulation circuit includes a circuit section that converts an instruction value as a voltage to a current, and a current mirror circuit that outputs the converted current to the electrodes. This configuration is typical for the electrical stimulation circuit.

Figure 9:
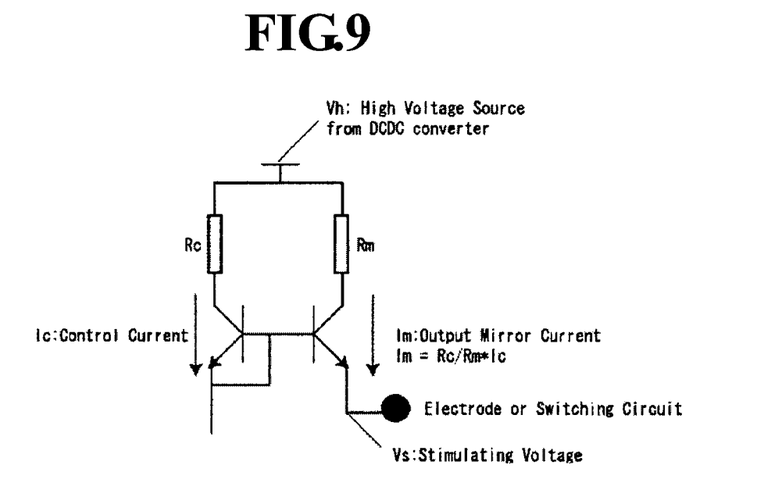
FIG. 9 is a view showing a current mirror circuit.

The current mirror circuit is shown in FIG. 9. This example is configured from a positive power supply and NPN transistors but the discussion described below is exactly the same when a negative power supply and PNP transistors are used. A control current Ic is amplified by a ratio Rc/Rm determined by a resistor Rc and a resistor Rm and is outputted to the electrodes or the switching circuit. When the voltage of a high-voltage generating circuit (DC-DC converter) is Vh and a voltage at an output section of the current mirror circuit is Vs, a voltage drop of Vh−Vs occurs. The voltage drop occurs at the current mirror transistors. This means that a Joule heat of Im×(Vh−Vs) is consumed by the transistors. This heat does not contribute to the stimulation and wastes completely. If the resistance of the skin is high, a voltage Vs required for the same quantity of stimulation current to flow becomes high. The voltage drop Vh−Vs therefore becomes small and unnecessary power consumption is reduced. However, if the resistance of the skin is low, the unnecessary power consumption conversely becomes large. Typical values for the current system are a power supply Vh of 350V, a stimulation current Im of 5 mA, and a stimulation voltage Vs changing in the order of from 200V to 330V depending on the state of the skin. In the worst case scenario, (350−200)×0.005=0.75 W is always unnecessarily consumed.

In order to resolve this problem, adjustment is always performed where the stimulation voltage Vs is measured, and the power supply voltage Vh is set slightly higher (ten to thirty volts) than the measured stimulation voltage. The time period for adjustment can be in the order of one second because variation of the resistance of the skin is sluggish. The power supply voltage is typically outputted by a DC-DC converter for which it is well-known that voltage regulation is straightforward. This adjustment is carried out using high-speed switching driving. There is therefore theoretically no unnecessary power consumption such as with the current mirror circuit described above. Many stimulation voltage measuring circuits have been introduced in the past in order to optimize the waveform of the stimulation by measuring the impedance of the skin but using this information to adjust the voltage source in order to reduce power consumption has not been tried.

To summarize, the electrical stimulation circuit includes means for measuring the stimulation voltage (stimulation voltage measuring circuit) and means for adjusting the power supply voltage. The power supply voltage is then set to a voltage a predetermined voltage V (for example, 10 to 30 volts) higher than the measured stimulation voltage by the means for adjusting the power supply voltage. The setting of the power supply voltage by the power supply voltage adjustment means is preferably carried out in a predetermined cycle (for example, one second).

[D] Technique for Converting Environmental Information into Electrical Stimulation Pulse

[D-1] Problems with the Present Series Systems

According to the stimulation system, with respect to a large number of electrical stimulation points, only one or some out of all electrodes are stimulated at a certain instant and a surface pattern is presented by scanning, or changing the stimulated electrode, like television scanning lines. However, in the case of visual sense-tactile sense conversion, the number of stimulation points is substantially larger than in the related art (for example, sixty-four points for the fingertip electrical stimulation device of the related art, and 512 points for the present forehead-mounted electrical stimulation systems). The time taken to scan also becomes huge as the number of stimulation points increases and the overall stimulation frequency also falls. The time taken for stimulation of one point is currently in the order of 100 microseconds. The time taken for 512 stimuli is therefore 51.2 milliseconds. Namely, the stimulation frequency is approximately 20 Hz.

It has been considered to make the stimulation pulse itself short but this is impractical because a high voltage is required in order to provide the same amount of energy for a shorter time. It is known that when the stimulation frequency falls below a 30 Hz, a characteristic "coarse feeling" occurs in the stimulation, and a strong feeling of unpleasantness occurs. The idea that the stimulation frequency is kept at a fixed frequency or more is essential. Further, it is difficult to present changes in intensity of sensations by changing the stimulation frequency because of lower stimulation frequency. This means that currently only binary information of 1 (stimulate) or 0 (do not stimulate) can be presented. This means that, for example, only binary values of black and white can be expressed when presenting image information.

[D-2] Resolving Technique of the Related Art: Parallel Stimulation Circuits

In the related art, resolving means were achieved by putting the stimulation circuits in parallel and increasing the number of points stimulated at the same time. For example, when the number of stimulation points is 512, the stimulation points are divided into eight modules of 64 points. At the same time, the scanning frequency can be increased by a factor of eight by carrying out stimulation at eight locations at the same time. However, eight times the amount of current is required in order to drive eight channels in parallel. The increase in the size of the high voltage power supply is comparatively large in proportion to the increase in the current capacity. Currently, the power supply for driving one channel is of a size that is the permissible limit for existing mobile device. This means that resolution of the problem with parallel stimulation is not possible.

[D-3] Increasing Frequency and Providing Intermediate Gradation by Implementing an Automatic Threshold Value Adjustment The number of times of electrical stimulation is adjusted by changing a determination function as to whether or not to carry out stimulation in real time to ensure that a certain maximum number of stimuli is not exceed. The maximum number of stimuli is set so that the time taken in overall stimulation does not exceed a certain time. In particular, when the stimulation frequency is 30 Hz or less (i.e. when a cycle is larger than 33 milliseconds), a strong sensation of unpleasantness occurs as described above. A typical value for the maximum number of stimuli in order to maintain the stimulation frequency at 30 Hz or more is therefore 33 milliseconds/100 microseconds=330 points, with 200 points or less taking into consideration overhead for communication etc. being an appropriate value.

A function for changing the stimulation determination function in real time is referred to as an automatic threshold value adjustment function. The following two effects are achieved by implementing the threshold value automatic adjustment function. First, a stimulation frequency of at least 30 Hz is ensured by suppressing the total number of stimuli. The first problem, "unpleasantness due to stimulation of less then 30 Hz" is therefore reduced as a result. Next, an intermediate gradation representation is implemented by increasing the number of stimuli at one point rather than just having the 0/1 representation of the related art.

In a typical implementation, first, the scanning frequency for the stimulation points in their entirety is fixed at 30 Hz (one cycle: 33 milliseconds). Stimulation intensity can be changed between 30 Hz to 210 Hz by stimulating each stimulation point between zero to seven times during this cycle. At this time, a function for performing adjustment using a threshold value automatic adjustment function is extended and adjustment takes place so that the total stimulation (number of times, not number of points) does not exceed the maximum stimulation number.

In this case, the expression of eight gradations of 0 to 7 is taken but further intermediate representations are also possible. This is implemented by the following algorithm.

Suppose that gradation to output at a certain cycle t is taken to be $X_t$ (a non-integral value between 0.0 and 7.0). $X_t$ is divided into an integer part $iX_t$ and a fractional part $dX_t$. Stimulation takes place in this cycle $iX_t$ times and the fraction part $dX_t$ is preserved. Suppose that at the next cycle, gradation to output is $X_{t+1}$, this is added to the remainder for the previous time. After this, this is similarly divided into an integer part and a fractional part with the number of times for the integer part being stimulated and the fractional part being saved. As a result of this repeating, it is possible to output intermediate gradation in a time-averaged manner. Presentation of a two-dimensional pattern is possible using grayscale with the above algorithm rather than using the two values of black and white.

Figure 15:
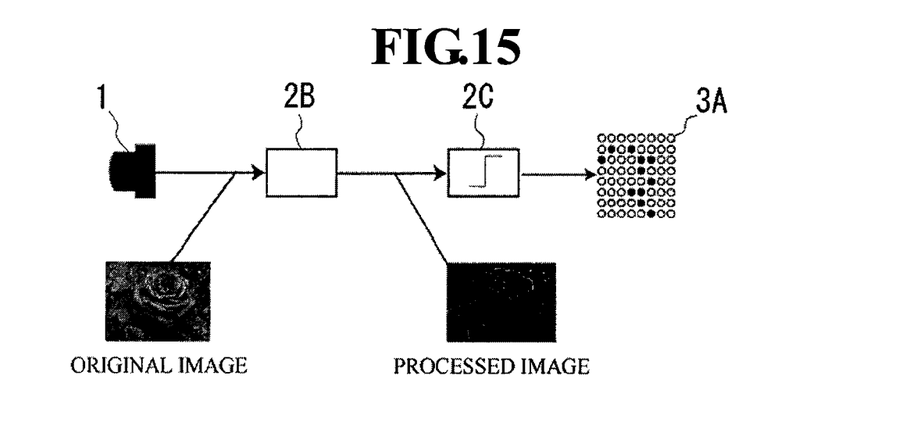
FIG. 15 is a view showing the relationship between a threshold value automatic adjustment function and an image processing function.

A description is given in the following of a threshold value automatic adjustment function. A relationship between the threshold value automatic adjustment function and other image processing functions is shown in FIG. 15. First, image data from the camera 1 is converted to processed images by the image processing unit 2B. The image processing is exemplified by edge extraction, contour extraction, "corner" extraction, color extraction, motion detection, and pattern recognition, etc. Electrical stimulation is carried out from the electrode matrix 3A based on the converted data. Threshold value control is then carried out at the threshold value automatic adjustment section 2C when electrical stimulation is carried out.

A description is now given of threshold value control at the threshold value automatic adjustment section 2C. In the following, suppose that representation is implemented using only the two values of stimulation performed/not performed.

A "stimulation determination function" is necessary to determine whether or not stimulation is carried out. For example, this is as follows.

"Stimulate when certain data is of a size of a threshold value or more. Do not stimulate when this is not the case"

$$N(i) = \begin{cases} 1 & (d(i) \geq \text{threshold}) \\ 0 & \text{otherwise} \end{cases} \quad [\text{Equation 1}]$$

Where, N(i) indicates the number of stimulations at the Ith point, d(i) is data, and "threshold" denotes the threshold value.

At this time, stimulation is carried out by scanning one point at a time. This means that if the "total number of stimulations" defined in the following equation is exceeded, the frequency of the stimulation lowers.

$$\sum_{i=1}^{M} N(i) \quad [\text{Equation 2}]$$

Where N(i) is the number of stimuli of the Ith electrode occurring in one cycle, and M is the total number of electrodes. Here, N(i) can only take the value 0 or 1. This means that the total number of stimuli is the same as the number of stimuli. This means that it is necessary to change the threshold value within the "stimulation determination function" in order to suppress the number of stimulation points. In the system shown in FIG. 15, the camera refresh rate is fixed. A new image is therefore inputted in a fixed time interval. For example, an image is updated every 33 milliseconds for a 30 fps camera. The electrical stimulation therefore has to finish scanning within 33 milliseconds. This means that stimulation can only take place 330 times when, for example, the time for one stimulation is 100 microseconds. This is the "maximum number of stimuli" permitted. In reality, the value is smaller because of overhead for communication etc.

For example, the following algorithm can be considered for adjustment of the threshold value of the stimulation determination function. First, an initial value for the threshold value is set by a user's input. When the number of times of stimulation for the stimulation determination function using this initial value does not exceed the maximum number of times of stimulation, the threshold value is not changed. However, when the number of times of stimulation exceeds the maximum number of times of stimulation, the threshold value is increased until the number of times of stimulation is less than the maximum number of times of stimulation. It is possible to obtain a minimum threshold value for ensuring that the number of times of stimulation is less than the maximum number of times of stimulation using the well-known binary tree method, etc.

When a large number of stimulations is permitted for one point and grey scale representation is implemented rather than black and white representation, the system configuration from the camera up to the stimulation electrodes is not changed and the camera refresh rate is also not changed. For example, the image is updated every 33 milliseconds. The intensity of stimulation at a certain stimulation point is defined as the number of times this point can be stimulated during a 33-millisecond cycle. The stimulation determination function is a function of original data having one or more parameters and defines the number of times of stimulation of each point within one cycle. The simplest example is, for example, as follows.

$$N(i) = \begin{cases} d(i) - \text{threshold} & (d(i) \geq \text{threshold}) \\ 0 & \text{otherwise} \end{cases} \quad [\text{Equation 3}]$$

The maximum number of stimulations permitted is determined as described above. The parameter (in this example, "threshold") for the stimulation determination function is then adjusted so that the "total number of stimuli" during one cycle does not exceed the maximum number of stimuli.

To summarize, the electro-tactile presentation apparatus includes an image capture section that captures images, an image processing unit that processes the acquired images, a control unit that generates a tactile presentation signal based on the information obtained by the image processing unit, an electrode array that generates tactile stimuli, and a switching circuit that switches each electrode between a power supply and ground. The control unit further includes a stimulation determination section (constructed from a stimulation determination function) that determines whether or not to carry out electrical stimulation, and a threshold value adjustment section (threshold value control section) that adjusts (controls) a threshold value of the stimulation determination section.

The threshold value adjustment section changes the threshold value of the stimulation determination function (function determining whether or not to carry out electrical stimulation) so that the number of stimuli occurring in a fixed time period (one cycle) does not exceed a predetermined maximum number of stimuli. It is then possible to ensure a preferred stimulation frequency (for example, at least 30 Hz or more) by suppressing the total number of stimuli.

An intermediate gradation representation is implemented by increasing the number of times of stimulation at one point. The scanning frequency for all of the stimulation points is fixed at a predetermined frequency or more (for example, 30 Hz or more). It is then possible to represent change in stimulation intensity from (scanning frequency×0) Hz to (scanning frequency×7) Hz by stimulating each stimulation point zero to seven times during this time. The threshold value of the stimulation determination means (stimulation determination function) is adjusted so that the total number of stimuli does not exceed the maximum number of stimuli.

[D-4] Achieving High-Quality for Spatial Feature Extraction

Figure 10:
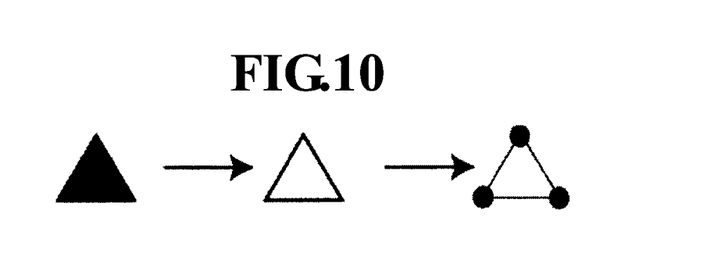
FIG. 10 is a view showing edge extraction, showing extraction of an "edge" using a simple edge extraction operation, and showing extraction of a "corner" to assist in recognition.

Currently, processing to enhance spatial edges of a pattern is carried out by extracting edges using a simple Laplacian operator when presenting a two-dimensional pattern. When, for example, a triangular shape is represented, the three edges are extracted and stimulated. However, this is insufficient and in order to improve sensory perception, it is necessary to enhance and stimulate the three "apexes" of the triangular shape (FIG. 10). In particular, in an environment where artificial objects are common, it is possible to automatically recognize straight lines, circles and ellipses using a "Hough transform" that is a typical image processing method and to obtain apex positions by calculating intersections of recognized lines. The presentation of high-quality sensations is then carried out by using the above technique to recognize apexes and the stimulating in an enhanced manner.

In particular, when the two-dimensional pattern is an image, extraction of a specific color, a specific brightness, and a specific time-varying change is important in practical terms in the present system. For example, in the case of utilization as sense of sight proxy system for a visually impaired person, by extracting specific colors, specific brightness, and specific time-varying change, it is possible to recognize the color of signals and flashing signals so as to present warnings to the user.

In addition, information that compares with a sense of sight can be presented using tactile stimulation of a lower spatial resolution compared to a sense of sight by recognizing and storing a specific pattern and representing the specific pattern using change in the type of stimulation. Of specific importance is the incorporation of a module for recognizing people's faces. In this way, the wearer can recognize known or yet-known people in surroundings.

[D-5] Response to Time-Varying Information

Figure 11:
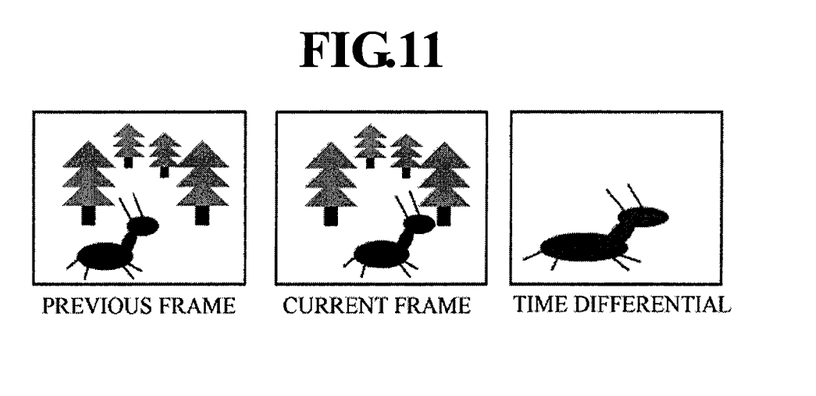
FIG. 11 is a view showing detection of changes in time due to time differential extraction of an image, where stimulation takes place after emphasizing moving objects.

A method for stimulating a time-varying (time differential) location in an enhanced manner simulates Meisner corpuscle activity that is one type of tactile receptor. This leads to the representation of high-quality sensations (FIG. 11). This itself can also be considered in related research.

Figure 12:
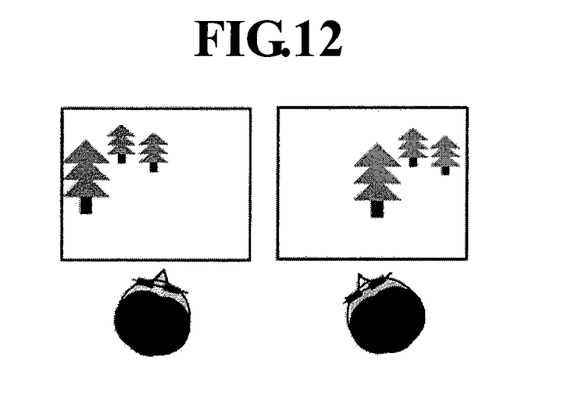
FIG. 12 is a view showing the movement of an entire image as a result of rotation of a person's head, which is targeted for deletion as an offset.
Figure 13:
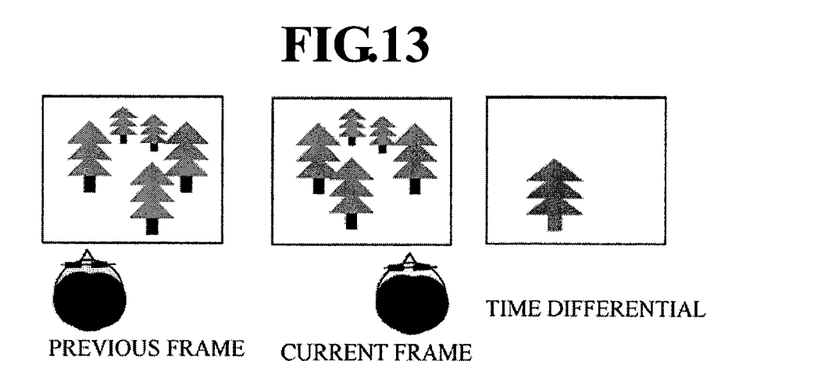
FIG. 13 is a view showing change of "see" due to a moving parallax, where the left side of the drawing is observed from the left, and the center of the drawing is observed from the right, and the image differential at the time of translational movement of the head becomes larger as the distance becomes closer to the target.

In the present system where a sensor is mounted on a person's head and the forehead is electrically stimulated, the characteristics are that it is important not to react to movement of the whole image. Namely, movement of the image as a whole is eliminated as an offset and only moving parts in the image are extracted. This means that changes to the image that inevitably occur at the forehead-mounted camera as a result of the observer moving their own head around are ignored and that objects moving in an external environment are enhanced (FIG. 12).

When cancellation of rotational movement of the head is incorporated, what happens when the head exhibits "translation motion"? At this time, by similarly compensating for movement of the image as a whole, it is possible to extract only objects that are in close proximity using a motion parallax (differences in "seeing" of three-dimensional objects using movement of a viewpoint). By utilizing this effectively, it is possible to acquire the detection of depth using translation movement of the head.

Figure 14:
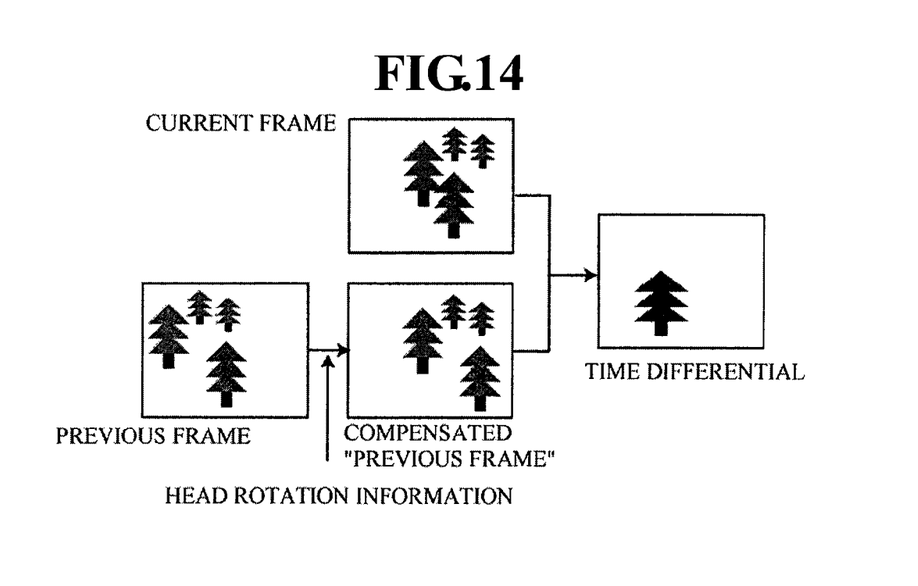
FIG. 14 is a view illustrating time differential extraction of an image, where changes in an image due to rotational movement are compensated for using image compensation using measurements of rotational movement of the head, and only changes to the image due to other causes are extracted.

As described above, a time differential is useful. However, the extent by which each pixel has moved corresponds to "correlation calculations" which require the largest amount of calculations in image processing. In order to suppress the load of the correlation calculation, flow vectors for the images due to rotation of the head are calculated using separate means and overall movement is then subtracted using this information in advance so as to make the size of the integration window used in the correlation arithmetic extremely small (=proportional to the assumed speed of movement). It is therefore possible to dramatically reduce the amount of calculation involved. If a binary output of "moved/didn't move" is simply adopted using a differential, the correlation calculation itself becomes unnecessary (FIG. 14). A method has been considered where a rotational acceleration sensor that measures head movement is built-in and compensation is performed using this information. Further, it has also been considered to use an artificial retina element with a movement extraction function.

In a preferred mode, the following image processing is carried out by an image processor. Image processing carried out by the image processing unit is by no means limited to the following, and can include image processing typically carried out in the image processing field.

(1) Achieving high-quality stimulation by spatial edge extraction and by detecting specific edges and apexes.
(2) Achieving high-quality stimulation by carrying out extraction of specific colors.
(3) Achieving high-quality stimulation by extracting specific brightness.
(4) Achieving high-quality stimulation by specific time-varying pattern extraction.
(5) Achieving high-quality stimulation through recognition and extraction of specific images, particularly faces of people.
(6) Achieving high-quality stimulation by detecting time-varying movement.
(7) The effects of image variation due to a person moving their head are eliminated by eliminating movement of the image as a whole as an offset. In one mode, an angular acceleration sensor is used in order to eliminate the effects of image variation due to rotational movement of the head. In a further mode, an artificial retina chip having a movement detection function is used.
(8) In a further mode, movement of the image as a whole is eliminated as an offset and remaining time-varying variation is displayed in an enhanced manner. The motion parallax is then enhanced by translational movement of the head and is taken as a cue for depth.

[E] Method for Acquiring Image Information while Using an Image Sensor as a Sensor

[E-1] Method for Presenting while Using a Wide-Angle Lens when Acquiring Images

The field of view is narrow so that it is necessary for the wearer to move their head frequently in order to obtain environment information for the whole of their surroundings. Further, because of narrower field of view, changes in the stimulation pattern represented as a result of movement of the head are acute and an unpleasant sensation is occurred. Further, supposing face to face communications between a visually impaired person wearing the present system and a healthy person, it is unconsciously assumed that both parties facing each other have a similar field of view. There is therefore the problem that it is difficult for the healthy person to communicate effectively with the person with impaired eyesight.

It is possible for the field of view to be made close to that of a healthy person (approximately 180 degrees when the pupil is not moved) by, for example, a wide-angle lens such as a fish-eye lens. If the field of view of the camera is made broader, the spatial resolution of the stimulation falls. However, a countermeasure is possible with respect to this problem where the ends of the image are compressed and representation takes place in the vicinity of the center at a high-resolution.

[E-2] Depth Detection and Presentation Using Focal Adjustment, a Compound Camera, and Measuring the Time-of-Flight Information presented to the wearer can be narrowed down by detecting depth information during image acquisition. For example, it is possible to prevent stimulation due to objects that are far away such as, for example, buildings etc. by just taking objects up to a few meters away from the wearer as targets of presentation. This method is preferable from the point of view of the safety of the wearer and it is assumed that many of the visual sense-tactile sense conversion apparatus provided up to this point are capable of sensing depth. However, depth information acquisition proposed in the related art has not yet been implemented to a level that can be used in real life.

It was therefore necessary to confirm the characteristics of the usage of our system. Measurement precision is not important. It can be considered sufficient if objects within the range of a few meters can be measured with a precision in the order of 0.5 meters. The following two straightforward techniques are therefore candidates.

Firstly, focus of a lens is used, with this typically being referred to as a lens focal point technique. It is possible to blur out anything other than a certain depth by using the lens. Our system extracts edges from the image for conversion to stimulation. Therefore, the fact that images at unnecessary distances are obscured during the image acquisition provides very good compatibility with the present system.

Secondly, a simple method also exists where illuminating light is projected from a camera and the brightness of the reflected light is then taken as is as depth information. This has the problem of depending on the optical characteristics of the illuminated target surface but has the substantial advantage that a broad depth can be obtained in an extremely straightforward manner.

It is also possible for any of the depth detection techniques other than the foregoing that are already commonly in use to be employed for presenting sensations depending on distance. Typical examples would be firstly, taking three dimensional measurements using two or more cameras, and another would be measurements using TOF (Time-of-Flight). In particular, when a compound camera is used, the foregoing object, "broad field of view", is achieved at the same time. In this case, three-dimensional depth detection is possible only for regions where the fields of view of each camera overlap but it is not considered to be a problem. This is exactly the same as when a person does with two eyes and people carry out their daily lives without hindrance with a stereoscopic vision of a center view where the fields of vision for the two eyes overlap.

In the above, depth is detected based on optical image acquisition but it is also possible to use depth detection employing ultrasonic waves. In particular, currently, compactness of depth detection devices that comprehend space in three-dimensions by analyzing waves reflected back from objects using one or a number of sound sources and a matrix of a number of small microphones are becoming widespread and are portable. The spatial resolution of depth detection based on ultrasonic waves is low compared to depth detection based on light. Currently, depth data of a few hundred×a few hundred points is acquired based on optical images but only depth data of a few tens×a few tens of depth data can be acquired using ultrasonic waves. However, with our system, the final number of tactile presentation points is small and the depth detection based on ultrasonic waves is also sufficient. Further, when ultrasonic waves are used, there is the advantage that use in darkness is also possible.

Finally, sensations that depend on distance are presented. For example, stronger stimuli are presented for distances that are closer. Alternatively, properties of the sensations caused by the stimuli are made to change depending on the distance.

To summarize, it is possible to ensure the same field of view as for a healthy person by using a wide-angle lens as the lens for the image acquisition unit. Falling of the spatial resolution of the stimuli due to the broader field of view of the camera can be countered by compressing the ends of the image and presenting the vicinity of the center using a high resolution. It is also possible to measure the depth using the focus adjustment of the camera and provide depth-dependent presentations based on this depth measurement.

It is further possible to simplify the system by taking only objects in the vicinity of the wearer as targets of sensation presentation using a fixed focal point lens suitable for a focal point of a distance up to a few meters from the wearer. It is also possible to perform depth-dependent presentation based on depth measurement integration by a plurality of cameras. Broadening the field of view using a plurality of cameras is also possible. It is further possible to perform depth-dependent presentation based on using the theory of TOF measurement.

INDUSTRIAL APPLICABILITY

The present invention is applicable to forehead-mounted electro-tactile displays, and more specifically is applicable to a portable visual sense proxy device.

The invention claimed is:

1. A forehead-mounted electro-tactile display comprising:
an electrode substrate provided with a plurality of stimulation electrodes;
a conductive gel layer positioned between the stimulation electrodes and the skin of a wearer;
a switching circuit section electrically connected to said stimulation electrodes;
a stimulation pattern generating section electrically connected to said switching circuit section;
wherein said plurality of stimulation electrodes have an electrode gap less than or equal to 5 mm,
wherein said conductive gel layer has a resistance value in a range between 100 and 1000 kΩcm, and
wherein said conductive gel layer has a thickness in a range between 0.3 and 2.0 millimeters.

2. The electro-tactile display of claim 1, wherein the thickness of said conductive gel layer is 0.5 to 1.0 millimeters.

3. The electro-tactile display of claim 1 further comprising:
a stimulation determiner that determines whether or not to carry out electrical stimulation based on a threshold value of a stimulation determination function; and
a threshold value adjuster that adjusts said threshold value of said stimulation determiner;
wherein said threshold value adjuster changes said threshold value so that the number of times of stimulation occurring in a fixed time period does not exceed a predetermined maximum number of stimuli.

4. The electro-tactile display of claim 3, wherein said threshold value adjuster ensures that the stimulation frequency is at least 30 Hz or more by suppressing the total number of stimuli occurring in a fixed time period.

5. The electro-tactile display of claim 3, wherein an intermediate gradation representation is implemented by increasing the number of times of stimulation at one point in a fixed time period.

6. The electro-tactile display of claim 1, wherein an electrical stimulation presentation board is comprised of said electrode substrate, said conductive gel layer, and said switching circuit section.

7. The electro-tactile display of claim 6, wherein said electrode substrate is a flexible substrate.

8. The electro-tactile display of claim 7, wherein said flexible substrate comprises at least one cut therein.

9. The electro-tactile display of claim 8, wherein a plurality of regions are defined by forming a plurality of cuts in transverse and vertical directions so as to leave the edges of said flexible substrate and a predetermined number of electrodes are provided at each region.

10. The electro-tactile display of claim 9, wherein a set of a switching circuit and a communication circuit is provided for each region, and wherein communication wiring for each communication circuit is provided at the edges.

11. The electro-tactile display of claim 8, wherein the flexible substrate includes a plurality of strip-shaped regions extending in a longitudinal direction of the electrical stimulation presentation board, with a predetermined number of electrodes being provided at each strip-shaped region.

12. The electro-tactile display of claim 6, wherein the electrical stimulation presentation board is provided with one or more elastic layers positioned at the surface side and/or the rear surface side of the electrode substrate.

13. The electro-tactile display of claim 12, wherein said elastic layer is an anisotropically conductive elastic layer provided at the surface side of the electrode substrate.

14. The electro-tactile display of claim 7, wherein the switching circuit section is provided at the flexible substrate.

15. The electro-tactile display of claim 7, wherein said electrical stimulation presentation board comprises a circuit substrate independent of the flexible substrate, and the switching circuit is provided at the circuit substrate.

16. The electro-tactile display of claim 1 further comprising:
   a stimulation voltage measurer for measuring stimulation voltage; and
   a power supply voltage adjuster for adjusting power supply voltage;
   wherein the power supply voltage is set to a voltage a predetermined voltage V higher than the measured stimulation voltage by said power supply voltage adjuster for adjusting power supply voltage.

17. The electro-tactile display of claim 1, wherein said display includes a stimulation emphasizer for emphasizing stimulation at time-varying locations and said stimulation emphasizer for emphasizing stimulation cancels changes to images caused by movement of the wearer and emphasizes an object moving in an external environment.

18. The electro-tactile display of claim 1 further comprising a depth detector for detecting depth so as to present sensations depending on distance.

19. The electro-tactile display of claim 1, wherein the gap between the stimulation electrodes is in the range 1 mm to 5 mm.

* * * * *